(12) United States Patent
Radisson

(10) Patent No.: US 6,365,748 B1
(45) Date of Patent: Apr. 2, 2002

(54) METHOD FOR PREPARING LINTITRIPT POTASSIUM SALT

(75) Inventor: Joël Radisson, Saubens (FR)

(73) Assignee: Sanofi-Synthelabo, Paris (FR)

(*) Notice: Subject to any disclaimer, the term of this patent is extended or adjusted under 35 U.S.C. 154(b) by 0 days.

(21) Appl. No.: 09/744,000

(22) PCT Filed: Jul. 15, 1999

(86) PCT No.: PCT/FR99/01724

§ 371 Date: Jan. 18, 2001

§ 102(e) Date: Jan. 18, 2001

(87) PCT Pub. No.: WO00/05233

PCT Pub. Date: Feb. 3, 2000

(30) Foreign Application Priority Data

Jul. 20, 1998 (FR) .............................. 98 09218

(51) Int. Cl.⁷ ............................................ C07D 417/12
(52) U.S. Cl. ..................................................... 548/181
(58) Field of Search ......................................... 548/181

(56) References Cited

U.S. PATENT DOCUMENTS

5,189,049 A  2/1993  Frehel et al. ................ 514/371

FOREIGN PATENT DOCUMENTS

EP  432 040    6/1996
WO  97/17064   5/1997

OTHER PUBLICATIONS

Derwent Patent Abstract No. 200013, 2000.

*Primary Examiner*—Laura L. Stockton
(74) *Attorney, Agent, or Firm*—Paul E. Dupont; Micahel D. Alexander

(57) ABSTRACT

A method for preparing the potassium dihydrate salt of 2-[[4-(2-chlorophenyl)-2-thiazolyl]carbamoyl]indole-1-acetic acid, by reacting 2-[[4-(2-chlorophenyl)-2-thiazolyl]carbamoyl]indole-1-acetic acid or its $C_1$–$C_4$ alkyl esters with potassium carbonate in a two phase solvent system comprising a mixture of water and an organic solvent which is only slightly miscible with water and optionally recrystallising the precipitated intermediate solvate from water and to the potassium dihydrate salt thus obtained.

28 Claims, No Drawings

METHOD FOR PREPARING LINTITRIPT POTASSIUM SALT

This application is a 371 of PCT/FR99/01724 filed Jul. 15, 1999.

The present invention relates to a method for preparing the potassium salt of 2-[[4-(2-chlorophenyl)-2-thiazolyl] carbamoyl]indole-1-acetate as well as the salts and solvates prepared by this method.

2-[[4-(2-chlorophenyl)-2-thiazolyl]carbamoyl]indole-1-acetic acid, represented by the formula (A),

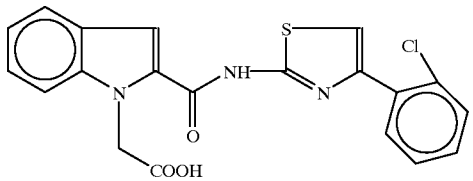

(A)

is a powerful antagonist of the A receptors of cholecystokinin ($CCK_A$ antagonist) described for the first time in EP-A-0 420 040 and also known by its International Common Designation "lintitript".

Lintitript has been studied in free acid form but, for the preparation of pharmaceutical compositions especially for parenteral usage, the use of its potassium salt has been considered advantageous (WO 97/17064).

In EP-A-0 420 040, lintitript is prepared by reaction of methyl 2-carboxyindol-1-ylacetate with 2-amino-4-(2-chlorophenyl)thiazole and by saponification of 2-[[4(2-chlorophenyl)-2-thiazolyl]carbamoyl]indole-1-acetate of methyl with sodium hydroxide and neutralization with hydrochloric acid. The lintitript thus obtained has, however, the drawback of absorbing hydrochloric acid, the said absorption taking place in non-stoichiometric quantities.

Attempts to produce salts of 2-[[4(2-chlorophenyl)-2-thiazolyl]carbamoyl]indole-1-acetic acid using an alkaline hydroxide, carried out in different solvents, notably in acetone or ethanol, have led to alkaline salts, either anhydrous or solvated, with a very variable solvent, water or organic solvent content. This variability of the composition of the salts is not acceptable for pharmaceutical products.

Furthermore, the use of alkaline hydroxides, quite strong bases, results in the extraction of more than one proton from the molecule (A) above, and leads to the formation of complex and, once again, not very reproducible mixtures of salts.

It has now been found that if 2-[[4(2-chlorophenyl)-2-thiazolyl]carbamoyl]indole-1-acetic acid or its $C_1$–$C_4$ allyl esters are treated with potassium carbonate in a solvent comprising a mixture of water and a solvent which is only slightly miscible with water, the potassium salt of lintitript can be isolated in the pure state and in a well-defined crystalline form by simple filtration.

Finally, it has been found that the potassium salt of lintitript can be prepared with excellent yields by in situ saponification, with potassium carbonate, of a ($C_1$–$C_4$) alkyl ester of 2-[[4(2-chlorophenyl)-2-thiazolyl]carbamoyl]indole-1-acetate in the mixture resulting from the reaction of 1-carboxyindolyl-1-acetate of ($C_1$–$C_4$) alkyl with 2-amino-4(2-chlorophenyl)thiazole, without therefore isolating the intermediate ester.

Thus, according to one of its aspects, the present invention relates to a method for preparing the potassium salt of lintitript, characterised in that 2-[[4-(2-chlorophenyl)-2-thiazolyl]carbamoyl]indole-1-acetic acid or its $C_1$–$C_4$ alkyl esters are treated with potassium carbonate in a two phase solvent system comprising a mixture of water and an organic solvent which is only slightly miscible with water, the precipitated intermediate solvate is optionally recrystallized in water and the potassium salt of lintitript thus obtained is isolated.

According to a preferred aspect, the method described above is carried out using a ($C_1$–$C_4$) alkyl ester, preferably the methyl ester, of 2-[[4-(2-chlorophenyl)-2-thiazolyl] carbamoyl]indole-1-acetate.

The reaction using 2-[[4-(2-chlorophenyl)-2-thiazolyl] carbamoyl]indole-1-acetic acid or its $C_1$–$C_4$ alkyl esters is carried out by mixing the product in the solvent which is only slightly miscible with water, adding potassium carbonate in water and heating the mixture for 1 to 30 hours. After cooling, the precipitated potassium salt of lintitript can be isolated by the customary techniques and optionally recrystallized to obtain an exceptionally pure product.

The method of the present invention, used on free lintitript or on one of its isolated $C_1$–$C_4$ alkyl esters or in the mixture resulting from the reaction of a ($C_1$–$C_4$) alkyl ester of 1-carboxyindolyl-1-acetate with 2-amino-4-(2-chlorophenyl) thiazole, leads in general to a hydrated salt in which the water of crystallization is well-defined. The potassium salt is in fact obtained in the form of the dihydrate. The anhydrous salt can be obtained by dehydration of the hydrate.

Potassium lintitript dihydrate constitutes a further aspect of the present invention.

As solvents which are only slightly miscible with water, use can be made of solvents which, with water, give a two phase system, for example ethers, high alcohols or, advantageously, a butanol or a ($C_4$–$C_6$)alkanone, such as methyl ethyl ketone or methyl isobutyl ketone. Among the butanols, 2-butanol and isobutanol are particularly advantageous solvents.

When n-butanol is used as the solvent which is only slightly miscible with water, a solvate of potassium lintitript with the butanol used and possibly with water may precipitate from the reactive medium. This solvate can be isolated and transformed into potassium lintitript dihydrate in the pure state. When n-butanol is used as the butanol, potassium 2-[[4-(2-chlorophenyl)-2-thiazolyl]carbamoyl]indole-1-acetate mono-n-butanolate monohydrate is obtained which precipitates and which is preferably isolated in order to allow it to be recrystallized in water and to allow very pure potassium 2-[[4-(2-chlorophenyl)-2-thiazolyl]carbamoyl] indole-1-acetate dehydrate to be obtained.

Potassium 2-[[4-(2-chlorophenyl)2-thiazolyl]carbamoyl] indole-1-acetate mono-n-butanolate monohydrate of formula (I),

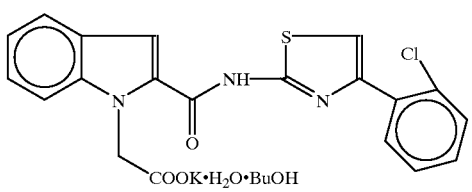

I in which Bu is n-butyl, represents a further object of the present invention.

On the other hand, when 2-butanol or isobutanol is used, no intermediate solvate is obtained, but potassium lintitript dihydrate is obtained directly and can in any case be recrystallized in water if a particularly pure product is required.

According to another of its aspects, the present invention relates to a method for preparing alkaline salts of lintitript, characterised in that a ($C_1$–$C_4$) alkyl ester of 2-carboxyindol-1-ylacetate of formula (II),

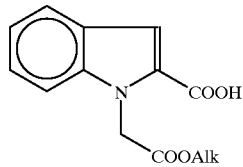

II in which Alk represents a ($C_1$–$C_4$) alkyl group, is treated with the 2-amino-4-(2-chlorophenyl)thiazole of formula (III),

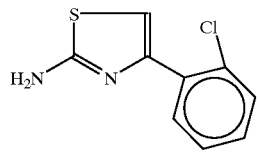

III the ($C_1$–$C_4$) alkyl ester of 2-[[4(2chlorophenyl)-2-thiazolyl]carbamoyl]indole-1-acetate thus obtained is saponified in situ with potassium carbonate in a two phase solvent system comprising a mixture of water and an organic solvent which is only slightly miscible with water, the precipitated intermediate solvate is optionally recrystallized in water and the potassium salt of lintitript thus obtained is isolated.

The reaction between the ($C_1$–$C_4$) alkyl ester of 2-carboxyindol-1-ylacetate and the 2-amino-4-(2-chlorophenyl)thiazole is carried out by activating the acid, for example using thionyl chloride in the presence of pyridine or dimethylformamide, and performing coupling with the amine in the presence of a coupling agent, such as 4-dimethylaminopyridine (DMAP), and a strong base, for example triethylamine, in an appropriate solvent. The compound thus obtained is either isolated according to the usual techniques, or directly subjected to the saponification reaction, this option being preferable from the practical and economic point of view. As the coupling solvent, tetrahydrofuran, methylene chloride or dichloromethane can certainly be used.

The preparation of the ($C_1$–$C_4$) alkyl ester of 2-carboxyindol-1-ylacetate of formula (II) is described in EP-A-0 420 040.

The preparation of the 2-amino-4-(2-chlorophenyl)thiazole of formula (III) is also described in EP-A-0 420 040, and in EP-A-0-192 998.

Also, when the saponification is performed on a ($C_1$–$C_4$) alkyl ester of 2-[[4-(2-chlorophenyl)-2-thiazolyl]carbamoyl]indole-1-acetate present in the mixture resulting from the reaction of ($C_1$–$C_4$) alkyl 1-carboxyindolyl-1-acetate with 2-amino-4(2-chlorophenyl)thiazole, methyl isobutyl ketone or a butanol is advantageously used as the solvent which is only slightly miscible with water.

The potassium lintitript dihydrate, which is obtained with high yields in a readily filterable, dense crystalline form, easily usable for the preparation of pharmaceutical forms both for oral administration and for parenteral administration, has characteristic infrared absorption maxima, notably at 3635 $cm^{-1}$, 1660 $cm^{-1}$,1595, $cm^{-1}$, 1550 $cm^{-1}$, 1310 $cm^-$, 1285 $cm^{-1}$ and 745 $cm^{-1}$.

The potassium lintitript dihydrate having the above characteristic infrared absorption maxima constitutes a preferred object of the present invention.

The potassium lintitript dihydrate has also been characterised by single crystal X-ray diffraction using a Rigaku AFC6S diffractometer, graphite monochromator and Cu-kα source. The crystallographic data, notably the interplanar distances (a, b, c), the angles (α, β, γ) and the volume of each unit cell are as follows:

| | | |
|---|---|---|
| a = 10.453 (2) Å | b = 13.171 (2) Å | c = 8.253 (1) Å |
| α = 107.89 (1) | β = 100.96 (1) | γ = 89.74 (2) |
| vol = 2631.44 Å$^3$ | | |
| Z = 8 | | |

The following examples illustrate the invention.

EXAMPLE 1

Potassium 2-[[4-(2-chlorophenyl-2-thiazolyl]carbamoyl]indole-1-acetate dihydrate 9.3 g (21.9 mmoles) of methyl-2-[[4-(2-chlorophenyl)-2-thiazolyl]carbamoyl-indole-1-acetate and 9.3 151 g (67.4 mmoles) of $K_2CO_3$ in 60 ml of isobutanol and 40 ml of water are heated under reflux for 3 hours. After cooling, the precipitate is filtered and rinsed with isobutanol and water. The above-captioned compound is obtained. M.Pt. 263–266° C. (dec).

EXAMPLE 2

Potassium 2-[[4-(2-chlorophenyl-2-thiazolyl]carbamoyl]indole-1-acetate dihydrate A mixture of 170 g of methyl-2-[[4-(2-chlorophenyl)-2-thiazolyl]carbamoyl-indole-1-acetate in 1 L of methyl ethyl ketone is heated under reflux for 15 hours with 500 ml of water and 2.8 equivalents of $K_2CO_3$. After cooling, the precipitate is filtered and rinsed with methyl ethyl ketone. The above-captioned compound is obtained. M.Pt. 263–266° C. (dec).

EXAMPLE 3

Potassium 2-[[4-(2-chlorophenyl-2-thiazolyl]carbamoyl]indole-1-acetate dihydrate 13.9 g (32.7 mmoles) of methyl-2-[[4-(2-chlorophenyl)-2-thiazolyl]carbamoyl-indole-1-acetate is heated under reflux for 3 hours with 15g of $K_2CO_3$ in 50 ml of methyl isobutyl ketone and 50 ml of water. After cooling, the precipitate is filtered and rinsed with isobutanol and water. The above-captioned compound is obtained.

EXAMPLE 4

Potassium 2-[[4-(2-chlorophenyl-2-thiazolyl]carbamoyl]indole-1-acetate mono-n-butanolate monohydrate 204.5 (0.50 mole) of methyl-2-[[4-(2-chlorophenyl)-2-thiazolyl]carbamoyl]indole-1-acetate is dissolved in 500 ml of 1-butanol and a solution of 208 g (1.5 mole) of alkaline carbonate in 700 ml of water added. The suspension is topped until the mass attained a temperature of 93° C., then heated under reflux for two hours. The precipitate is filtered and washed with 400 ml of butanol, then with 900 ml of water. The above-captioned compound is obtained. M.Pt. 250–260° C. (dec).

EXAMPLE 5

Potassium 2-[[4-(2-chlorophenyl-2-thiazolyl]carbamoyl]indole-1-acetate dihydrate 100 g of the compound of Example 1 is heated in 500 ml of water. The solution is left to cool and the precipitate formed is filtered. 85.8 g of the above-captioned compound is obtained. M.Pt. 263–266° C. (dec).

EXAMPLE 6

Potassium 2-[[4-(2-chlorophenyl-2-thiazolyl]carbamoyl]indole-1-acetate dihydrate 9 g of product of Example 2 is recrystallized in 60 ml of 1-butanol containing 18% water. The precipitate formed is then recrystallized, with no intermediate drying, in 90 ml of water, without topping. The above-captioned compound is obtained in a particularly pure form, at 99.95%.

Potassium 2-[[4-(2-chlorophenyl-2-thiazolyl]carbamoyl]indole-1-acetate dihydrate 9.3 g (21.9 mmoles) of methyl-2-[[4-(2-chlorophenyl)-2-thiazolyl]carbamoyl-indole-1-acetate and 9.3 g (67.4 mmoles) of $K_2CO_3$ are heated under reflux for 3 hours in 60 ml of 2-butanol and 40 ml of water. After cooling, the precipitate is filtered and rinsed with 2-butanol and water. The above-captioned compound is obtained. M.Pt. 263–266° C. (dec).

What is claimed is:

1. Potassium 2-[[4-(2-chlorophenyl)-2-thiazolyl]carbamoyl]indole-1-acetate dihydrate.

2. Potassium 2-[[4-(2-chlorophenyl)-2-thiazolyl]carbamoyl]indole-1-acetate mono-n-butanolate monohydrate.

3. Potassium 2-[[4-(2-chlorophenyl)-2-thiazolyl]-carbamoyl]indole-1-acetate dihydrate according to claim 1 which displays infrared absorption maxima at 3635 cm$^{-1}$, 1660 cm$^{-1}$, 1595 cm$^{-1}$, 1550 cm$^{-1}$, 1310 cm$^{-1}$, 1285 cm$^{-1}$ and 745 cm$^{-1}$.

4. A method for preparing potassium 2-[[4-(2-chlorophenyl)-2-thiazolyl]carbamoyl]indole-1-acetate dihydrate which comprises treating 2-[[4-(2-chlorophenyl)-2-thiazolyl]carbamoyl]indole-1-acetic acid or its $C_1$–$C_4$ alkyl esters with potassium carbonate in a two phase solvent system comprising a mixture of water and an organic solvent which is only slightly miscible with water.

5. A method according to claim 4 wherein the solvent which is only slightly miscible with water is selected from the group consisting of the ethers, the butanols and the ($C_4$–$C_6$) alkanones.

6. A method according to claim 5 wherein methyl isobutyl ketone or methyl ethyl ketone is used as the solvent which is only slightly miscible with water.

7. A method according to claim 5 wherein a butanol is used as the solvent which is only slightly miscible with water.

8. A method according to claim 4 wherein the product obtained is recrystallized from water.

9. A method according to claim 7 wherein the product obtained is recrystallized from water.

10. A method according to claim 4 wherein the reaction is carried out using a ($C_1$–$C_4$)alkyl ester of 2-[[4-(2-chlorophenyl)-2-thiazolyl]carbamoyl]indole-1-acetate.

11. A method according to claim 10 wherein the product obtained is recrystallized from water.

12. A method according to claim 10 wherein methyl-2-[[4-(2-chlorophenyl)-2-thiazolyl]carbamoyl]indole-1-acetate is used as the ($C_1$–$C_4$)alkyl ester of [[4-(2-chlorophenyl)-2-thiazolyl]carbamoyl]indole-1-acetate.

13. A method according to claim 10 wherein the solvent which is only slightly miscible with water is selected from the group consisting of the ethers, the butanols, and the ($C_4$–$C_6$) alkanones.

14. A method according to claim 12 wherein the product obtained is recrystallized from water.

15. A method according to claim 12 wherein the solvent which is only slightly miscible with water is selected from the group consisting of the ethers, the butanols, and the ($C_4$–$C_6$) alkanones.

16. A method according to claim 15 wherein methyl isobutyl ketone or methyl ethyl ketone is used as the solvent which is only slightly miscible with water.

17. A method according to claim 15 wherein a butanol is used as the solvent which is only slightly miscible with water.

18. A method according to claim 17 wherein the product obtained is recrystallized from water.

19. A method according to claim 13 wherein methyl isobutyl ketone or methyl ethyl ketone is used as the solvent which is only slightly miscible with water.

20. A method according to claim 13 wherein a butanol is used as the solvent which is only slightly miscible with water.

21. A method according to claim 20 wherein the product obtained is recrystallized from water.

22. A method for preparing potassium 2-[[4-(2-chlorophenyl)-2-thiazolyl]carbamoyl]indole-1-acetate dihydrate which comprises reacting a 2-carboxyindol-1-ylacetate of formula (II),

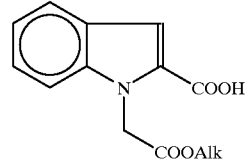

(II)

in which Alk represents a ($C_1$–$C_4$) alkyl group, with the 2-amino-4-(2-chlorophenyl)thiazole of formula (III),

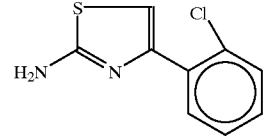

(III)

and saponifying the ($C_1$–$C_4$) alkyl ester of 2-[[4-(2-chlorophenyl)-2-thiazolyl]carbamoyl]indole-1-acetate in situ with potassium carbonate in a two phase solvent system comprising a mixture of water and an organic solvent which is only slightly miscible with water.

23. A method according to claim 22 wherein methyl-2-carboxyindolyl-1-acetate is used as the initial ($C_1$–$C_4$) alkyl ester of 2-carboxyindolyl-1-acetate.

24. A method according to claim 22 wherein methyl isobutyl ketone, methyl ethyl ketone or a butanol is used as the solvent which is only slightly miscible with water.

25. A method according to claim 22 wherein the product obtained is recrystallized from water.

26. A method according to claim 23 wherein methyl isobutyl ketone, methyl ethyl ketone or a butanol is used as the solvent which is only slightly miscible with water.

27. A method according to claim 24 wherein the product obtained is recrystallized from water.

28. A method according to claim 26 wherein the product obtained is recrystallized from water.

* * * * *

UNITED STATES PATENT AND TRADEMARK OFFICE
CERTIFICATE OF CORRECTION

PATENT NO.    : 6,365,748 B1                                    Page 1 of 1
DATED         : April 2, 2002
INVENTOR(S)   : Joël Radisson It is certified that error appears in the above-identified patent and that said Letters Patent is hereby corrected as shown below:

Column 5,
Line 23, insert the title -- EXAMPLE 7 -- above the words "Potassium 2-[[4-(2-chlorophenyl-2-thiazolyl]"

Signed and Sealed this

Third Day of June, 2003

JAMES E. ROGAN
*Director of the United States Patent and Trademark Office*